(12) United States Patent
Xiao

(10) Patent No.: US 9,498,508 B2
(45) Date of Patent: Nov. 22, 2016

(54) PHARMACEUTICAL COMPOSITION FOR TREATING CANCERS AND PREPARATION METHOD THEREFOR

(71) Applicant: Mingchun Xiao, Dongguan (CN)

(72) Inventor: Mingchun Xiao, Dongguan (CN)

( * ) Notice: Subject to any disclaimer, the term of this patent is extended or adjusted under 35 U.S.C. 154(b) by 0 days.

(21) Appl. No.: 14/846,786

(22) Filed: Sep. 6, 2015

(65) Prior Publication Data

US 2015/0374778 A1  Dec. 31, 2015

Related U.S. Application Data

(63) Continuation-in-part of application No. PCT/CN2013/080936, filed on Aug. 6, 2013.

(30) Foreign Application Priority Data

Mar. 11, 2013 (CN) .......................... 2013 1 0078199

(51) Int. Cl.

| | | |
|---|---|---|
| A01N 65/00 | (2009.01) |
| A61K 36/9068 | (2006.01) |
| A61K 36/752 | (2006.01) |
| A61K 36/804 | (2006.01) |
| A61K 36/85 | (2006.01) |
| A61K 36/884 | (2006.01) |
| A61K 36/888 | (2006.01) |
| A61K 36/8884 | (2006.01) |
| A61K 36/8888 | (2006.01) |
| A61K 36/8945 | (2006.01) |
| A61K 36/8988 | (2006.01) |
| A61K 36/8998 | (2006.01) |
| A61K 36/9062 | (2006.01) |
| A61K 36/9064 | (2006.01) |
| A61K 36/9066 | (2006.01) |
| A61K 36/46 | (2006.01) |
| A61K 36/481 | (2006.01) |
| A61K 36/484 | (2006.01) |
| A61K 36/53 | (2006.01) |
| A61K 36/54 | (2006.01) |
| A61K 36/575 | (2006.01) |
| A61K 36/68 | (2006.01) |
| A61K 36/71 | (2006.01) |
| A61K 36/714 | (2006.01) |
| A61K 36/734 | (2006.01) |
| A23F 3/16 | (2006.01) |
| A61K 36/076 | (2006.01) |
| A61K 36/232 | (2006.01) |
| A61K 36/233 | (2006.01) |
| A61K 36/284 | (2006.01) |
| A61K 36/48 | (2006.01) |
| A61K 36/482 | (2006.01) |
| A61K 36/532 | (2006.01) |
| A61K 36/535 | (2006.01) |
| A61K 36/538 | (2006.01) |
| A61K 36/539 | (2006.01) |
| A61K 36/65 | (2006.01) |
| A61K 36/66 | (2006.01) |
| A61K 36/88 | (2006.01) |
| A61K 36/8905 | (2006.01) |

(Continued)

(52) U.S. Cl.
CPC ........... *A61K 36/9068* (2013.01); *A23F 3/163* (2013.01); *A61K 36/07* (2013.01); *A61K 36/076* (2013.01); *A61K 36/12* (2013.01); *A61K 36/185* (2013.01); *A61K 36/21* (2013.01); *A61K 36/232* (2013.01); *A61K 36/233* (2013.01); *A61K 36/236* (2013.01); *A61K 36/237* (2013.01); *A61K 36/258* (2013.01); *A61K 36/268* (2013.01); *A61K 36/284* (2013.01); *A61K 36/46* (2013.01); *A61K 36/48* (2013.01); *A61K 36/481* (2013.01); *A61K 36/482* (2013.01); *A61K 36/484* (2013.01); *A61K 36/515* (2013.01); *A61K 36/53* (2013.01); *A61K 36/532* (2013.01); *A61K 36/535* (2013.01); *A61K 36/538* (2013.01); *A61K 36/539* (2013.01); *A61K 36/54* (2013.01); *A61K 36/575* (2013.01); *A61K 36/65* (2013.01); *A61K 36/66* (2013.01); *A61K 36/68* (2013.01); *A61K 36/71* (2013.01); *A61K 36/714* (2013.01); *A61K 36/734* (2013.01); *A61K 36/752* (2013.01); *A61K 36/804* (2013.01); *A61K 36/85* (2013.01); *A61K 36/88* (2013.01); *A61K 36/882* (2013.01); *A61K 36/884* (2013.01); *A61K 36/888* (2013.01); *A61K 36/8884* (2013.01); *A61K 36/8888* (2013.01); *A61K 36/8905* (2013.01); *A61K 36/8945* (2013.01); *A61K 36/8988* (2013.01); *A61K 36/8998* (2013.01); *A61K 36/906* (2013.01); *A61K 36/9062* (2013.01); *A61K 36/9064* (2013.01); *A61K 36/9066* (2013.01)

(58) Field of Classification Search
CPC ....................................................... A61K 36/00
USPC .......................................................... 424/725
See application file for complete search history.

(56) References Cited

U.S. PATENT DOCUMENTS

2015/0374778 A1* 12/2015 Xiao .................... A61K 36/752
424/195.15

*Primary Examiner* — Michael Meller

(74) *Attorney, Agent, or Firm* — Wayne & King LLC

(57) ABSTRACT

A pharmaceutical composition for treating cancers and preparation method thereof. Said composition for treating cancers contains Chinese medicinal materials including Rhizoma Pinelliae, Rhizoma Arisaematis, Rhizoma Gastrodiae etc., and said preparation method is in accordance with a conventional Chinese medicinal preparation method, manufacturing said composition to form any one of the ordinary oral preparations.

1 Claim, No Drawings

(51) Int. Cl.
*A61K 36/906* (2006.01)
*A61K 36/07* (2006.01)
*A61K 36/12* (2006.01)
*A61K 36/185* (2006.01)
*A61K 36/21* (2006.01)
*A61K 36/236* (2006.01)
*A61K 36/237* (2006.01)
*A61K 36/258* (2006.01)
*A61K 36/268* (2006.01)
*A61K 36/515* (2006.01)
*A61K 36/882* (2006.01)

PHARMACEUTICAL COMPOSITION FOR TREATING CANCERS AND PREPARATION METHOD THEREFOR

CROSS-REFERENCE TO RELATED APPLICATIONS

This application is a continuation-in-part of International Patent Application No. PCT/CN2013/080936 with an international filing date of Aug. 6, 2013, designating the United States, now pending, and further claims priority benefits to Chinese Patent Application No. 201310078199.5 filed Mar. 11, 2013. The contents of all of the aforementioned applications, including any intervening amendments thereto, are incorporated herein by reference.

TECHNICAL FIELD

The present invention included in the medical care field, can diagnose and treat cancers and multiple diseases for clinic in medicine. The present invention refers to pharmaceutical compositions for treating cancers, in particular pharmaceutical compositions for treating and preventing cancers and preparation method thereof, regarding Chinese herbal medicine as the bulk drug.

BACKGROUND OF THE INVENTION

Cancer is the primary cause of death in the worldwide. It is estimated by World Health Organization that there would be 84 million people died of cancer the period from 2005 to 2015 without intervention. Deaths from cancer amounted to 7.4 million (about 13% of all deaths). Lung, stomach, liver, colon and breast cancer cause the most cancer deaths each year. More than 70% of death caused by cancer happened in low-income and middle-income countries. Deaths from cancer worldwide are projected to continue to rise to 12 million in 2030.

Up to now, the existing dozens of anti-cancer drugs all can not cure the cancer. Neither chemotherapy nor radio therapy has remarkable effect on cancer treatment. there exists toxic side effects and other deficiencies, patients react strongly after medications, and has a high degree of pain. Even worse, it accelerates patient's death. Surgical treatment in early stage is easily to recur and metastasize and the effect is also not obvious.

SUMMARY OF THE INVENTION

A technical problem to be solved by the present invention is to overcome above deficiencies by providing a pharmaceutical composition for treating cancers of a significant effect, low cost, low toxicity.

In the process of studying theory of traditional Chinese medicine (TCM), I found the analysis of *Record of Headache in Famous Doctors Medical Record Analysis of Past Dynasties* by Yuansu Zhang, the famous doctor in Jin dynasty. He said "Combining Jueyin with Taiyin disease are called wind-phlegm headache". I studied his theory carefully and analyzed "Liver Channel of Foot-Jueyin and Spleen Channel of Foot-Taiyin". Finally I made the conclusion that what Yuansu Zhang called "Jueyin Disease" is combined lung cancer with brain tumor, and "Taiyin Disease" is liver cancer, based on theories of TCM and western medicine. So "wind-phlegm headache" is the lung cancer combined with brain tumors accompanying liver cancer metastasis. Yuansu Zhang can cure the "wind-phlegm headache" by Yuhu Pills, combined with the prescription thereof, I found Decoction of Rhizoma Pinelliae, Atractylodes Macrocephala and Rhizome Gastrodiae is a basic prescription for treating lung cancer and brain tumors with liver cancer metastasis. Besides, I found the "Fungus" is one of major factors of cancer through further analysis. My discovery process is as follows:

1. Etiological Analysis

Yuhu Pills (Ingredient: rhizoma arisaematis, rhizome pinelliae, rhizoma gastrodiae, ginger) can acquire a good result for treating lung cancer and brain tumors with liver cancer metastasis in *Record of Headache* of Zhang Yuansu, a medical scientist in Jin dynasty. Yuhu Pills, the modified Decoction of Rhizoma Pinelliae, Atractylodes Macrocephala and Rhizoma Gastrodiae (Ingredient: rhizoma pinelliae, rhizoma gastrodiae, atractylodes macrocephala, poria cocos, dried tangerine peel, licorice), are mainly used for treating "the wind-phlegm syndrome" Based on the prescription thereof, I have found what ancients called "phlegm-dampness" refers to the lung cancer, "dampness" means cancer cell, "damp evil" means carcinogen "the wind-phlegm syndrome" means brain metastasis from lung cancer.

The opinion of disease enters by the mouth has been known to everyone in China, which means the disease may enter the body through three ways: from oral cavity to digestive tract, from throat to lung, from nasal cavity to upper respiratory tract. As the only organ which is open to the external environment, lung is the most vulnerable to be infected. So the primary lesion of ancient cancers is in the lung at most cases. That's why ancients named lung cancer as "phlegm-dampness", "damp evil" as carcinogen and "wind" as cancer cell metastasis.

I think just using Yuhu Pills to treat headache is not enough. Because the rhizoma pinelliae and rhizoma gastrodiae in Yuhu Pills are mainly used for treating lung cancer combined with brain tumor, mainly targeting liver meridian. While liver cancer is the disease of spleen meridian, as a result, I think the specific and targeted drugs should be added to Yuhu Pills. And "phlegm-dampness" is primary lung cancer, so the conclusion that what ancients said "syndrome of phlegm stagnation" is metastatic tumor from lung cancer. "Damp evil" is a carcinogenic factor, so "dampclearing prescription" is a antineoplastic drug. Peptic Powder, a representative prescription for treating spleen meridian, is a basic prescription for treating metastatic liver cancer by analyzing "dampclearing prescription".

And "damp evil" is a carcinogenic factor, so what is "damp evil"?

Chinese physicians regarded the "damp evil" as "yin pathogen". "Yin" means female, and it can also be understood as no sunshine (i.e. no oxygen), so mycosis, a disease that women is easily to be attacked and a pathogenic bacteria without oxygen, is a common disease of female vaginitis. Both liver meridian and spleen meridian are yin meridians, and bacteria without oxygen exist in liver and spleen meridian, so both of which are veins. So what Chinese ancient physicians said twelve meridians are actually blood circulation system composed of three veins and three arteries on hand, as well as three veins and three arteries on foot as starting point and ending point, which is also in compliance with theories of Yin-Yang, Yin is without oxygen and Yang is with oxygen, which means Yin is vein and Yang is artery. So "yin pathogen" is virus, bacillus, anaerobic bacteria, mold and others exist in veins. That virus can result in cancer has become a consensus, and the understanding of mold is under study.

Modern medicine has proved people are easy to affect liver cancer if they eat peanuts, rice and other foods infected by mold due to the carcinogenesis of aflatoxin, Dermatology and Venereology has also proved that *candida albicans* can cause the affection of skin, mucosa, viscera, skeleton and brain via external or internal source. In the view of modern medicine, *candida albicans* is one of normal bacterial parasite in human, as conditioned pathogen, it is nonpathogenic and can coexist with human body. I think it is wrong. It is corroding our body slowly, rather than static. And it will become active when immunity is decreasing and symptoms become evident.

Mold prefers to live in acid environment than alkaline environment, prefer to low temperature than high temperature. That is why cancer will cause the body physical condition to become acidic and cold. Mold also thrives in where the blood flow is slow, so it is critical to do more exercise to accelerate blood circulation and heat the body to improve the living environment of mold for hard retention and reproduction. Mold like humid environment, so it is good for the reproduction of mold in spring, as well as foods are easy to be infected by mold in spring, especially a large number of mold and viruses are contained in humid air, which adds the inducement again.

I think what Chinese ancients said "pathogenic qi" and "dampness" refer to "moldy taste", and i.e. "spleen meridian" is a vein throughout the digestive system of splenic vein, while "stomach meridian" is the artery throughout the digestive system, "liver meridian" is vein circulation from hallux toe of foot up to top of the head throughout portal vein of liver, and the corresponding artery is "gallbladder channel". The artery paralleled with "kidney channel" is "bladder meridian". In ancient Qingming Festival, the custom of "eliminating evil" is to fume mold in the house dead by burning "folium artemisiae argyi". Drinking yellow wine and eating alkali zongzi in "Dragon Boat Festival" are to constrain the growth of mold in the body by fermentative yellow wine and alkaline water. It can be confirmed what Chinese physicians said "damp evil" mainly refers to mold by analysis of these ancient words and phrases. So I suggest to add PH value of blood and contents check of mold in blood detection such that cancer can be found as early as possible. And mold exists in veins and has maternal and infants infectivity, which is the root cause of cancer with familial incidence.

There is a TCM prescription Er Chen Decoction (Ingredient: rhizoma pinelliae, dried tangerine or orange peel, poria cocas, licorice, dark plum, dried ginger), in this prescription, the longer storing of dried tangerine or orange peel and rhizoma pinelliae, the better. That's because they will become sweet-scented after long-time storage rather than moldy, which explains they generates anti-fungus microorganism during long-time fermentation. That's why mature vinegar, fruit vinegar, sweet rice wine yoghurt and others through natural fermentation can play a role of health protection and treatment, microorganism generated by them kill mold parasited in liver and other viscera, thereby recovering digestive function of liver and other viscera. It has also proved from the side that many chronic diseases and cancers of human are mainly caused by anaerobic bacteria, dominated by mold.

In Chinese physicians' view, cold can be divided into"anemofrigid cold" and "anemopyretic cold", which is reasonable. Chinese physicians regard there are six germs: wind, cold, heat, damp, dry and fever. "Heat evil" refers to germs which can cause body heat and high fever: "cold evil" refers to germs which can cause body chill; "damp evil" refers to germs which can exist in blood, mucus and other liquids.

Modern science finds that infection of virus and bacteria will cause high fever, so "anemopyretic cold" is caused by virus in the air and others, i.e. it is cold caused by virus. I think "anemofrigid cold" is infected by mold in the air, symptoms include fever, headache, snuffle, body aches or sneeze and runny nose. And the clinical symptoms will be more severe with age growth, which is because mold in the body become more and more with age growth. Chinese physicians regarded the "cold evil" as "Yin Pathogen". So "cold evil" is also mold, "wind-cold-effusing medicinal" should be used to treat "anemofrigid cold".

In Chinese physicians' view, That spleen is afraid of damp and kidney is afraid of cold refers to spleen meridian is afraid of "damp evil" and kidney channel is afraid of "cold evil", which is a process of mold from quantitative change to qualitative change. Usually liver is the first organ to be infected and at that time patients show symptoms of "damp evil". As the disease progresses, the mold infects the kidney to cause the decrease of kidney function, patients would show the symptoms of "cold evil", which is the beginning of canceration, so cold body is a process of mold from quantitative change to qualitative change.

*Treatise on Febrile and Miscellaneous Diseases* by Zhongjing Zhang from Han dynasty, is a medical thesis about various diseases caused by "cold evil". That is a medical thesis of various diseases after infecting "mold". Wars and natural disasters happened frequently in the warring states and the qin-han period, which results in the death of large quantities of human beings and animals, and a mass of mold induced by the death of human beings and animals propagated, more human beings affected mold to death because these mold further polluted air, water and food heavily. So that is why there are old saying go "After the war, there will be a great plague" and "After the war, there will be a great plague". Like the appearance of French perfume, the great plague happened in Europe was also caused by mold, so French found the flowers with fantastic aroma can resist disease. During the process of fighting against the diseases, Chinese ancient physicians also found the role of "resolving dampness with aromatics"

So I think "damp evil" refers to mold, virus, bacillus and others, of which mold is the main; meanwhile "cold evil" refers to mold only, so combined with the analysis of both, mold is the main cause of cancer, and the culprit of non-accidental death of human beings and animals. Air condition is an environment to induce mold, there exists many factors to induce mold growth in the enclosed environment of air-conditioned room, such as coldness, stuffiness, and slow blood circulation due to sitting, that is why modern people appear various chronic diseases and various cancers frequently and early.

Of course, nowadays, more and more factors contribute to the formation of cancers due to pollution of industry and chemicals and variation of various virus. However, the overuse of antibiotics and hormone, air conditioned environment and the air pollution, mold is still the main cause of cancer. Mold can spread through aerial infection, contact infection, and blood infection, so it may infect the whole body. Mold will multiply at where the blood circulation is slow, from quantitative change to qualitative change and finally cause the cancer.

Two. The pathological Change Caused by Mold and Chinese Medicine Treatment Methods Mold, with high toxicity, is a chronic corrosive process for whole body of human beings and animals. From the life span of animals, we can come to the conclusion that if the life condition of mold in the body during the lifespan can't be improved, then the life span of animal will be just a decade. It will affect every organs in our body slowly in a latent way and finally cause death due to failure of organs function. Below I'm going to analyze the mold canceration (mildew) of whole body and Chinese medicine treatment method from top to toe.

1. Analysis of Mold Infection of the Brain and Head

Human beings are easy to infect anemofrigid cold because a mass of mold are existed in dark and damp environment, besides, blood vessel of brain is very rich, so mold is easy to enter into brain, that is why cardia-cerebrovascular disease happens so frequently.

The mold infection of the brain results in the necrosis of brain tissue, nerve, blood vessel and cell, many diseases such as headache, nerve paralysis, mental abnormity, high blood pressure, epilepsy, alzheimer's disease, brain infarction, cerebral apoplexy will be happened, and finally brain tumor and cerebral hemorrhage will be formed to cause death. It also explains why cerebral hemorrhage and cerebral apoplexy are easy to be happened at night, that is because mold stuck in the head are easy to propagate due to low temperature of patients and slow blood circulation, which accelerates the erosion of blood vessel and nerve in the brain. Rhizoma gastrodiae can be used to treat high blood pressure and IT is a kind of antifungal medicine that targets to brain, so the root cause of high blood pressure is in the head. The disturbance of blood circulation in the head will result in autoimmune response generated by human beings, which equals to the principle of hydraulic pump, vascular dilation drugs to lower the blood pressure are easy to cause the insufficiency of brain blood supply, thereby causing alzheimer's disease. Some eye diseases, such as cataract, glaucoma and pterygium are also caused by the mold infection of eyes. Many oral diseases, such as the toothache, tooth decay and dental ulcer are also related to the mold infection. Many drugs can not enter into brain due to brain barrier. So Treatise on the Spleen and Stomach by Donghuan Li said. The headache caused by the disease of Foot-Tai Yin can be cured only by rhizoma pinelliae; the giddiness and dizzy can be treated only by rhizoma gastrodiae. So they are used to be monarch drugs. Ancient Chinese physicians had already realized the blood brain barrier, so they made the conclusion that rhizoma gastrodiae was targeted to the brain, while rhizoma pinelliae can be used to treat whole body except the head. Combined with rhizoma gastrodiae and rhizoma pinelliae, the systematic fungal infection can be treated, and it is also anti-cancer drug of the whole body. In fact, rhizoma gastrodiae, bombyx batryticatus, arisaema cum bile and notopterygium are all medicinal materials that target to the head. Rhizoma gastrodiae combined with Ligusticum wallichii, drugs for activating blood and alleviating pain and the guiding drugs radix angelicae can have a good effect for treating the mold infection of brain. The representative prescription is Decoction of Rhizoma Pinelliae, Atractylodes Macrocephala and Rhizoma Gastrodiae (Ingredient: rhizoma pinelliae, rhizoma gastrodiae, atractylodes macrocephala, poria cocos, dried tangerine peel, licorice), rhizoma pinelliae and rhizoma gastrodiae are monarch drugs in the prescription, and arisaema cum bile is added into them to make Yuhu Pills, which is key drug to treat cancer. The chemical components of rhizoma pinelliae, arisaema cum bile and rhizoma gastrodiae contain volatile oil and alkaloid, which play an important role because mold prefers acid than alkali.

2. The Mold Infection of the Respiratory Tract

Mold infection of the respiratory tract will cause chronic rhinitis, nasosinusitis, chronic pneumonia and finally the lung cancer to death. Rhizoma gastrodiae and arisaema cum bile are antifungal drugs targeted to the upper respiratory tract, while rhizoma pinelliae and Dried Tangerine Peel are antifungal drugs targeted to the lower respiratory tract, besides, they have broad-spectrum anti-fungal role. The representative prescription Erchen Decoction (Ingredient: rhizoma pinelliae, dried tangerine peel, poria cocos, licorice, dark plum, dried ginger). An antifungal prescription targeted at respiratory tract comprise the medicine materials in Erchen Decoction together with notopterygium, radices sileris, purple perilla, tenuifolia, cassia twig, radix angelicae, asarum, magnolia flower, fructus xanthii and others. It is a basic prescription for anemofrigid cold, chronic rhinitis and nasosinusitis.

Erchen Decoction has many other curative effects when combined with some other medicinal materials. When combined with rhizoma atractylodis and magnolia officinalis, it can treat the hepatitis, hypohepatia, liver cancer, pancreatitis, and pancreatic cancer: when combined with arisaema cum bile and trichosanthes kirilowii Maxim, it can treat the acute bronchitis and pneumonia; when combined with dried ginger and asarum, it can treat nephritis, nephrotic syndrome and others; when combined with rhizoma gastrodiae and bombyx batryticatus, it can treat the brain tumor; when combined with semen raphani and fructus hordei germinatus, it can treat the gastric ulcer and gastric cancer and other gastrointestinal diseases; when combined with rhizoma cyperi, pericarpium citri reticulatae viride and radix curcumae, it can treat the hepatic calculus and others; when combined with seaweed, kelp and oyster, it can treat the lymphadenectasis. So Erchen Decoction, as the monarch drug, is not only a basic prescription for preventing and treating cancer, but also antineoplastic drugs for whole body.

Yuhu Pills, Erchen Decoction and Decoction of Rhizoma Pinelliae, Atractylodes Macrocephala and Rhizome Gastrodiae are different prescriptions whose common monarch drugs are rhizome pinelliae and rhizoma gastrodiae. The compatible drugs are mainly dried tangerine peel, I think dried orange peel is generally used for early disease, while fructus aurantii immaturus is better when tumor happened, and dried tangerine peel is used for terminal disease.

3. Analysis of Mold Infection of Viscera

The mold infection of viscera such as liver will decline the function of liver and kidney like indigestion, sugar diabetes, hyperlipemia, sicca syndrome, climacteric syndrome, hypoimmunity, cirrhosis and finally cancer to cause death. Some flavoring agents such as rhizoma atractylodis, magnolia officinalis, amomun kravanh, katsumadai seed and amomum tsao-ko are anti-fungal drugs targeted at liver, gallbladder, spleen and pancreas. The representative prescription is Peptic Powder (Ingredient: rhizoma atractylodis, magnolia officinalis, dried orange peel, licorice) and Decoction of Rhizoma Pinelliae and Magnolia Officinalis (Ingredient: rhizoma pinelliae, magnolia officinalis, poria cocos, ginger, perilla leaf). The effective components of rhizome atractylodis and magnolia officinalis is volatile oil, which can inhibit the fungus.

In Chinese medicine prescription, drugs of Warming Cold-damp are targeted at anticancer prescription for kidney. Common warming yang herbs such as dried ginger, cassia twig, monkshood are combined with drugs for invigorating spleen and eliminating dampness such as poria cocas and atractylodes macrocephala to make a prescription. The representative prescription is Zhenwu Decoction (Ingredient: poria cocos, paenoy, atractylodes macrocephala, ginger, monkshood) and Bixie Fengqing Powder (Ingredient: alpinia oxyphylla, yam rhizome, acorus tatarinowii, lindera aggregate), add "yang-tonifying drug", Erchen Decoction, achyranthes bidentata for invigorating blood circulation and eliminating stasis into these prescriptions can have a good effect on chronic nephritis and uraemia. Achyranthes bidentata is a drug for invigorating blood circulation targeted at kidney. And monkshood, the life-saving drug, is used for warming kidney and treating uraemia, of which aconitine is chemical component to kill mold due to strong alkalinity.

Yam rhizome, poria cocos, grifola, rhizoma alismatis, asarum, monkshood, cinnamon and dried ginger are not also anti-fungal drugs targeted at urinary system, but also diuretics. The representative prescription is Wulin Powder (Ingredient: grifola, poria cocos, atractylodes macrocephala, poria cocos and cassia twig).

"Digestant drugs" such as hawthorn, medicated leaven, radix aucklandiae, fructus amorni and fructus hordei germinatus are targeted at gastrointestinal tract. The representative prescription Zhishi Xiaopi Pills (Ingredient: dried ginger, honey-fried licorice root, poria cocos, atractylodes macrocephala, rhizoma pinelliae, ginseng, magnolia officinalis, fructus aurantii immaturus, coptidis rhizoma) can prevent and treat stomach cancer. Spleen-strengthening Bolus (Ingredient: atractylodes macrocephala, radix aucklandiae, coptidis rhizoma, licorice, poria cocos, ginseng, medicated leaven, dried orange peel, fructus amomi, fructus hordei germinatus, hawthorn, yam, myristica fragrans) can be used to prevent and treat gastrointestinal cancer.

4. The Mold Infection of Bones and Joints

The mold infection of bones and joints can cause osteoporosis, osteonecrosis, joint deformity, redness and swelling of joints, and joint failure. "Rheumatalgia" is mold infection of bones and nerves. Chinese medicine prescription Decoction of Notopterygium for Rheumatism (Ingredient: notopterygium, angelica pubescens, ligusticum, radix sileris, licorice, fructus viticis, ligusticum wallichii) can be used to treat disease that cancer cell metastasis cause body aches. From the properties of notopterygium, radix sileris and ligusticum, they are all wind-cold-effusing medicinals, and also in accordance with characteristics that cancer patient is with cold body. The body aches of cancer patient caused by the metastasis of cancer cells is actually the rheumatalgia. In the prescription, notopterygium and angelica pubescens are monarch drugs. Notopterygium can be used to head, neck and shoulder aching, namely pain from rheumatism of upper body; angelica pubescens can be used to treat joint pain of wrist, knee, legs and feet through entry into kidney channel. The body aches can be treated if combined with them. The notopterygium is very effective in dredging vessel and relieving pain, especially in treating headache by producing heat and thus dredge vessel. Modern medical science has proved that notopterygium has the effect of inhibiting fungus and bacterium burger. And ligusticum wallichii is a drug for invigorating blood circulation and eliminating stasis targeted at upper body.

Angelicae Pubescentis and Loranthi Decoction (Ingredient: angelica pubescens, parasitic loranthus, eucommia ulmoides, achyranthes bidentata, asarum, gentiana macrophylla, poria cocos, cinnamon heart, radix sileris, ligusticum wallichii, ginseng, licorice, angelica sinensis, paenoy, dried radix rehmanniae), a representative prescription of anticancer cell metastasis and repair function of liver, lung and kidney, can be used for the treatment of function recovery phase.

5. I think the main symptom of early mold infection of viscera is various stones such as hepatic calculus, kidney stone, urinary calculus and joint calculus, so drugs such as christina loosestrife herb, semen plantaginis, rhizoma cibotii, achyranthes bidentata, paenoy, radix curcumae combined with licorice, astragalus and other tonifying Qi drugs are targeted at these stones.

6. Mold Infection of Skin and Mucosa

The mold infection of skin and mucosa can cause various pruritus, such as dermatophytosis, tinea of feet and hands, eczema, rubella, seasonal dermatitis in spring and summer, neurodermatitis and so on. That is why various pruritus happened frequently between spring and summer. Spring is a active phase for mold propagation. "Folium artemisiae argyi" is used to bathe in Chinese ancient Qingming Festival, which illustrates that folium artemisiae argyi has a role of anti-fungus. Chinese physicians are fond of taking a bathe with "flowers" to keep in good health, which is a reflection of "resolving dampness with aromatics". The wind-cold-effusing medicinals radix sileris and tenuifolia can be used to treat various pruritus cutanea.

7. Mold Infection of Reproductive System

Mold infection can significantly influence the reproductive system. Mammitis, hyperplasia of mammary glands, mammary cancer, fibroid, endometrial diseases, cervix diseases are all related to mold infection. In the view of traditional Chinese medicine, gynecological diseases belong to the diseases of liver meridian, so these diseases can be treated as liver diseases.

In summary, mold infection has tremendous effect on human health through analysis of the pathological change process caused by mold infection of whole body and Chinese medicine treatment method. The mold will infect the liver, spleen and kidney to cause edema, and develop to cold body to cause indigestion due to stomach cola, finally kidney cold to form cancer. Mold is real killer to non-accidental death of human beings. These drugs are of strong smell or fragrance mostly through analysis of properties and chemical components of above drugs, the properties of these drugs are warm, containing volatile oil and alkaloid mostly, which are not only chemical components to inhibit mold, but also chemical components of antineoplastic drugs. Decoction of Rhizome Pinelliae, Atractylodes Macrocephala and Rhizoma Gastrodiae or Erchen Decoction is a basic prescription to treat cancer for whole body through analysis. Peptic Powder is a prescription targeted at treating cancer in digestive tract, and Decoction of Notopterygium for Rheumatism is a prescription targeted at treating cancer cell metastasis, Angelicae Pubescentis and Loranthi Decoction is used for the treatment of function recovery phase, and Zhenwu Decoction and Bode Fengqing Powder can be used to treat cancer in urinary system, digestant drugs can be used to prevent and treat gastrointestinal cancer. And combined with Wuling Powder for inducing diuresis to reduce edema, a treatment plan for treating cancer of whole body can be obtained, it is also a basic medication principle of all cancers and all diseases caused by mold. Meanwhile, therapeutic methods such as physical therapy, massage and acupuncture therapy can play a role of auxiliary therapy and help to diffuse mold cluster.

Three. Pharmaceutical Composition Preparation Methods

Following are a new prescription combined based on above etiological analysis and therapeutic method of Chinese medicines.

1. A new combined prescription based on addition and subtraction of Chinese medicine prescription Decoction of Rhizoma Pinelliae, Atractylodes Macrocephala and Rhizome Gastrodiae, and Peptic Powder, rhizoma pinelliae 3~50 dosages, rhizoma arisaematis 3~50 dosages, rhizoma gastrodiae 3~50 dosages, poria cocas 3~50 dosages, dried tangerine peel 3~50 dosages, atracylodes macrocephala 3~50 dosages, licorice 3~50 dosages, ginger 3~50 dosages, ligusticum wallichii 3~50 dosages, radix angelicae 3~50 dosages, rhizome atractylodis 3~50 dosages, bark of magnolia 3~50 dosages.

2. A new combined prescription based on addition and subtraction of Chinese medicine Decoction of Notopterygium for Rheumatism, and Angelicae Pubescentis and Loranthi Decoction: notopterygium 3~50 dosages, angelica pubescens 3~50 dosages, asarum 1~10 dosages, ligusticum 3~50 dosages, radix sileris 3~50 dosages, fructus viticis 3~50 dosages, parasitic loranthus 3~100 dosages, eucommia ulmoides 3~50 dosages, achyranthes bidentata 3~50 dosages, gentiana macrophylla 3~50 dosages, cinnamon heart 1~25 dosages, ginseng 3~50 dosages, angelica sinensis 3~50 dosages, paenoy 3~50 dosages, dried radix rehmanniae 3~50 dosages, and astragalus 3~100 dosages.

3. A new combined prescription based on addition and subtraction of Chinese medicine prescription Decoction of Rhizoma Pinelliae, Atractylodes Macrocephala and Rhizome Gastrodiae, Peptic Powder, Decoction of Notopterygium for Rheumatism, and Angelicae Pubescentis and Loranthi Decoction: rhizoma pinelliae 3~50 dosages, rhizoma arisaematis 3~50 dosages, rhizoma gastrodiae 3~50 dosages, poria cocos 3~50 dosages, dried tangerine peel 3~50 dosages, atracylodes macrocephaly 3~50 dosages, licorice 3~50 dosages, ginger 3~50 dosages, ligusticum wallichii 3~50 dosages, radix angelicae 3~50 dosages, rhizome atractylodis 3~50 dosages, bark of magnolia 3~50 dosages, notopterygium 3~50 dosages, angelica pubescens 3~50 dosages, asarum 1~10 dosages, ligusticum 3~50 dosages, radix sileris 3~50 dosages, fructus viticis 3~50 dosages, parasitic loranthus 3~100 dosages, eucommia ulmoides 3~50 dosages, achyranthes bidentata 3~50 dosages, gentiana macrophylla 3~50 dosages, cinnamon heart 1~25 dosages, ginseng 3~50 dosages, angelica sinensis 3~50 dosages, paenoy 3~50 dosages, dried radix rehmanniae 3~50 dosages, and astragalus 3~100 dosages.

4. A new combined prescription based on the addition and subtraction of Chinese medicine prescription Zhenwu Decotion, Bixie Fenqing Powder and Wuling Powder: monkshood 3~50 dosages, rhizoma cibotii 3~50 dosages, rhizoma alismatis 3~50 dosages, grifola 3~50 dosages, christina loosestrife herb 3~100 dosages, semen plantaginis 3~50 dosages, yam rhizome 3~50 dosages, acorus tatarinowii 3~50 dosages, alpinia oxyphylla 3~50 dosages, and magnolia flower 3~50 dosages.

5. A new combined prescription based on the addition and subtraction of Chinese medicine prescription Zhishi Xiaopi Pill and Spleen-strengthening Pill: lindera aggregate 3~50 dosages, radix aucklandiae 3~50 dosages, medicated leaven 3~30 dosages, fructus amomi 3~50 dosages, fructus hordei germinatus 5~100 dosages, hawthorn 3~50 dosages, myristica fragrans 3~50 dosages, fructus aurantii immaturus 3~50 dosages, and radix curcumae 3~50 dosages.

6. A new prescription based on the combination of above Method 3, 4 and 5: rhizoma pinelliae 15 dosages, rhizoma arisaematis 15 dosages, 6, 6, 6. The new combined prescription based on the combination of Method 3 Method 4 and Method 5 is: rhizoma gastrodiae 15 dosages, poria cocos 15 dosages, dried tangerine peel 10 dosages, atractylodes macrocephaly 20 dosages, licorice 9 dosages, ginger 10 dosages, rhizoma atractylodis 15 dosages, bark of magnolia 15 dosages, notopterygium 10 dosages, angelica pubescens 10 dosages, asarum 3 dosages, ligusticum wallichii 10 dosages, radix angelicae 10 dosages, ligusticum 8 dosages, radix sileris 12 dosages, fructus viticis 5 dosages, parasitic loranthus 20 dosages, eucommia ulmoides 15 dosages, achyranthes bidentata 15 dosages, gentians macrophylla 10 dosages, cinnamon heart 5 dosages, ginseng 10 dosages, angelica sinensis 10 dosages, paenoy 15 dosages, dried radix rehmanniae 15 dosages, astragalus 20 dosages, monkshood 10 dosages, rhizoma cibotii 15 dosages, rhizoma alismatis 15 dosages, grifola 10 dosages, christina loosestrife herb 20 dosages, semen plantaginis 15 dosages, yam rhizome 15 dosages, acorus tatarinowii 15 dosages, alpinia oxyphylla 15 dosages, magnolia flower 15 dosages, lindera aggregata 15 dosages, radix aucklandiae 9 dosages, medicated leaven 6 dosages, fructus amomi 10 dosages, fructus hordei germinatus 20 dosages, hawthorn 15 dosages, myristica fragrans 10 dosages, fructus aurantii immaturus 10 dosages, and radix curcumae 15 dosages.

The above six pharmaceutical compositions of the present invention add various conventional auxiliary materials as different dosage forms needed like disintegrants, lubricants and adhesives to prepare any kind of oral preparations, including pills, capsules, tablets, granules or oral liquids, syrup and other dosage forms. It can prepare pieces of Chinese medicine directly to make health tea.

Besides, the above six pharmaceutical compositions of the present invention can extract effective chemical composition such as alkaloid, volatile oil and other powerful chemicals from crude drug to prepare biological agents, including oral preparation (like capsules, tablets, granules or oral liquids), injection (including various doses) and drugs for external use (including health products).

The above pharmaceutical compositions of the present invention are applicable to medical drugs, health food, health products, animal drugs, and animal feed.

Advantages of the present invention are as follows:

1. Compliance with national formulary.
2. Easy to use, safe.
3. Accurate curative effect and scarce side-effects.
4. Easy to get crude drugs and easy to generalize.
5. Mature, simple and cheap production process of Chinese patent medicine.
8. Mature raw material extraction technique of biological agents.
7. Clinical human trial over 2,000 years from Qin dynasty to now proved the accurate curative effect.

Five. Treatment Experience

I am a sufferer of lung cancer with brain tumor, and 1 also feel swelling pain of right abdomen. Although I didn't make a definite diagnosis, I am very clear about my situation.

I am always in poor health. It will cost about half a month to cure my cold with western medicine. I got stomach and duodenal hemorrhagein in 2007 and since then I have tried to improve my health with traditional Chinese medicine, felt much better and I became convinced in Chinese medicine. But the mistaken chronic pharyngitis and rhinitis still happened frequently. Besides, the headache and insomnia can't be treated. Later, I got headache frequently, especially the left forehead. Then I realized that the cause of my headache was not chronic rhinitis but lung cancer with brain tumor. I felt nervous and didn't want to go to hospital because of fear. So I determined to find a treatment method in Chinese medicine, I borrowed a book from library and discovered that my situation was similar to the one in *Record of Headache by Yuansu Zhang in Famous Doctors Medical Record Analysis of Past Dynasties*. Then I confirmed my situation and tried Decoction of Rhizoma Pinelliae, Atractylodes Macrocephala and Rhizoma Gastrodiae on Feb. 21, 2011. I had remarkable improvement after trying the prescription, I began to sneeze and the left nasal cavity became running nose continually, which makes me experience the miracle of Chinese medicine. But I'm not so confident because I learned western medicine after all, so one day later I went to the hospital and let one Chinese medicine physician make the prescription based on the book. The Chinese medicine physician added notopterygium, radix sileris, asarum, radix angelicae, fructus xanthii and other drugs for driving away cold based on Decoction of Rhizoma Pinelliae, Atractylodes Macrocephala and Rhizoma Gastrodiae after knowing my situation and feeling my pulse. With these medicinal herbs, I ran at nose and felt extremely hot at left lung. (My former symptoms happened mainly in head). At the fifth day, I went to hospital again and the physician changed the rhizoma pinelliae, arisaema cum bile, and notopterygium to drugs for nourishing yin, such as radix pseudostellariae and adenophora stricta. The following days were the most suffering days. After stop using the rhizoma pinelliae, I could still feel the heat of lung, and my cough became even more serious. It felt like sputum can't be discharged. Fortunately there was aster that can make me feel better. Then I tried the Angelicae Pubescentis and Loranthi Decoction due to arthralgia. It felt me better after eating because the body aches moved down. Then I realized that I should use rhizome pinelliae and arisaema cum bile. The disease must be treated by rhizoma pinelliae. So I went to buy drugs again, and the future treatment tended to be stable. The first course of treatment cost about 3 months and I felt that my tumor in the left brain was almost disappeared and right nasal cavity was almost no running nose. Sputum in the lungs was also produced. However, after that I couldn't stop taking the medicine, otherwise I would feel the heat in my lung and have a lot of sputum. And sputum was easy to be produced after taking medicine. I could feel that the cancer had lymphatic metastasis, hepatic metastasis and intestinal metastasis because my liver and kidney weakness and I could feel the swelling pain and dull pain from right lower abdomen. It didn't become better until 1 year later I found Peptic Powder. In conclusion, I couldn't stop using rhizoma pinelliae and rhizoma gastrodiae, and drugs for nourishing yin can't be used. In fact, heat in the lungs at that time was normal reaction of drugs. But I still thank the physician Quan very much for letting me know the role of wind-cold-effusing medicinal.

When thinking of my process of treating cancer, comparing with the popular way to treat cancer, I think using the "clearing away heat and toxic material" medicine is incorrect because only warm can beat the coldness. The chemotherapy and radioactive therapy will only accelerate the death of patients, because chemotherapy cause hepatotoxicity and kidney failure. As for early surgery, I don't think it is a good way. In ancient China, Huatuo and Bianque were two very famous doctors good at surgery. However during the process of development, the surgery became less and less important in traditional Chinese medicine. I think the reason is the physicians discovered the incredible power of natural herbs, besides, surgery is not good for natural herbs to play its role due to natural structure failure of human beings. From my sputum discharging experience, it is regular for self-discharging sputum of human beings, I can be very sensitive to feel its movement. I think I will seize opportunity to write down my whole treatment process.

In conclusion, the main prescription used to treat cancer is Decoction of Rhizome Pinelliae, Atractylodes Macrocephala and Rhizome Gastrodiae. In this way, the lung cancer with brain tumor can be discharged from the body just as nasal discharge, and lung cancer cell can be discharged as sputum. In fact sneeze is a behavior to discharge the mucus of upper respiratory tract and cough is a behavior to discharge the mucus of lower respiratory passage by human beings own immunity.

REFERENCES

1. Zhongjia Deng National Advanced Planned Textbook for TCM Colleges and Universities, *Prescription*, Chinese Traditional Medicine Press, September 2009
2. Xuemin Gap, National Advanced Planned Textbook for TCM Colleges and Universities, *Traditional Chinese Pharmacology*, Chinese Traditional Medicine Press. September 2009
3. Fayin Yi, Fanglin Hu, *Famous Doctors Medical Record Analysis of Past Dynasties*, Medical Publishing Bureau of Chemical Industry Press. April 2008.
4. Wanshan Hao, *Treatise on Febrile Diseases*, People's Medical Publishing House. (1st edition), February 2013.
5. Dong Zhang, *Patent Research Of Traditional China Medicine Internationalization*, Intellectual Property Publishing House, June 2012

I claim:
1. A tablet or capsule for treating cancer consisting essentially of therapeutically effective amounts of an extract of rhizoma pinelliae, an extract of rhizoma arisaematis, an extract of rhizoma gastrodiae and an extract of ginger.

* * * * *